(12) United States Patent
Kuo (10) Patent No.: US 7,777,021 B2
(45) Date of Patent: Aug. 17, 2010

(54) GYLCERALDEHYDE-3-PHOSPHATE DEHYDROGENASE PROMOTER AND HETEROLOGOUS GENE EXPRESSION

(75) Inventor: Chun-Yi Kuo, Taipei County (TW)

(73) Assignee: Mycomagic Biotechnology Co., Ltd., Taipei County (TW)

( * ) Notice: Subject to any disclaimer, the term of this patent is extended or adjusted under 35 U.S.C. 154(b) by 425 days.

(21) Appl. No.: 12/021,219

(22) Filed: Jan. 28, 2008

(65) Prior Publication Data

US 2009/0193544 A1 Jul. 30, 2009

(51) Int. Cl.
C07H 21/04 (2006.01)
C12N 15/80 (2006.01)
(52) U.S. Cl. .................. 536/24.1; 800/279; 800/287; 800/288; 800/297; 435/69.1; 435/320.1
(58) Field of Classification Search .................. None
See application file for complete search history.

(56) References Cited

OTHER PUBLICATIONS

Henrich et al., EST database Accession No. CR476185, Rat Lion Rattus norvegicus cDNA clone.*
An et al, Mol Gen Genet (1986) 203:245-250.*
Grant A Bitter et al.,; Expression of interfoeron-gamma from hybrid yeast GPD promoters containing upstream regulatory sequences from the GAL1-GAL10 intergenic region; Journal; 1988; pp. 193-207; vol. 69; Gene; Elsevier Science Publishers B.V.
Frank Doring et al.,; Use of the Glyceraldehyde-3-phosphate Dehydrogenase Promoter for Production of Functional Mammalian Membrane Transport Proteins in the Yeast *Pichia pastoris*; Journal; 1998; pp. 531-535; vol. 250, No. 2; Biochemical and Biophysical Research Communication; Academic Press.
Peter Eriksson, et al.,; Cloning and characterization of GPD2 . . . ; Journal;1995; pp. 95-107; vol. 17, No. 1; Molecular Microbiology; Blackwell Science Ltd.
P. Guerche et al.,; Direct Gene Transfer By Electroporation in Brassica Napus; Journal; 1987; pp. 111-116; vol. 52; Plant Science; Elsevier Scientific Publishers Ireland Ltd.
Martin C. Harmsen et al.,; Sequence analysis of the glyceraldehyde-3-phosphate dehydrogenase genes from the basidiomycetes Schizophyllum commune . . . ; Journal; 1992; pp. 447-454; vol. 22; Current Genetics; Springer-Verlag.
Tatsuya Hirano et al.,; Isolation and Characterization of the Glycerldehyde-3-phosphate Dehydrogenase Gene of *Lentinus edodes*; Journal; 1999; pp. 1223-1227; vol. 63, No. 7; Biosci Biotechnol Biochem.
T. Hirano et al.,; Efficient transformation of the edible basidiomycete *Lentinus edodes* with a vector using a glyceraldehyde-3-phosphate dehydrogenase promoter to hygromycin B resistance; Journal; 2000; pp. 1047-1052; vol. 263; Mol Gen Genet; Springer-Verlag.
N. Juge et al.,; Secretion, purification, and characterisation of barley . . . ; Journal; 1998; pp. 385-392; vol. 49; Appl Microbiol Biotechnol; Springer-Verlag.
Mogens Kilstrup et al.,; Rapid genome walking . . . ; Journal; 2000; pp. e55 i-iv; vol. 28, No. 11; Nucleic Acids Research; Oxford University Press.
T. M. Klein et al., High-velocity microprojectiles for delivering necleic acids into living cells; Journal; May 7, 1987; pp. 70-73; vol. 327; Nature Publishing Group.
Chun-Yi Kuo et al.,; Cloning of glyceraldehyde-3-phosphate dehydrogenase gene and use of the gpd promoter for transformation in *Flammulina velutipes*; Journal; 2004; pp. 593-599; vol. 65; Appl Microbiol Biotechnol.
G. Neuhaus et al.,; Transgenic rapeseed plants obtained by the microinjection of DNA into microspore-derived embryoids; Journal; 1987; pp. 30-36; vol. 75; Theor. Appl. Genet.
P.J. Punt.,et al.,; Transformation of Aspergillus based on the hygromycin B resistance marker from *Escherichia coli*; Journal; 1987; pp. 117-124; vol. 56; Gene; Elsevier Science Publishers B.V.
B. Ruiz-Diez; Strategies for the transformation of filamentous fungi; Journal; 2002; pp. 189-195; vol. 92; J Appl Microbiol.; The Society for Applied Microbiology.
M.D. Van De Rhee et al.,; Transformation of the cultivated mushroom; Journal; 1996; pp. 252-258; vol. 250; Mol Gen Genet.; Springer-Verlag.
Ana Vassileva et al.,; Expression of hepatitis B surface antigen in the methylotrophic yeast *Pichia pastoris* using the GAP promoter; Journal; 2001; pp. 21-35; vol. 88; J Biotechnology; Elselvier Science B.V.

* cited by examiner

*Primary Examiner*—Eileen B O Hara
(74) *Attorney, Agent, or Firm*—WPAT, P.C.; Anthony King (57) ABSTRACT

The invention relates to discovery of an isolated glyceraldehyde-3-phosphate dehydrogenase promoter in *Pleurotus* and a construct comprising the promoter of the invention operably linked to a heterologous transcribable polynucleotide molecule.

16 Claims, 4 Drawing Sheets

```
  1  GGATCGGCCGTCTCGTACCCAGTAATGCACTTGAAGTCGGAGGCGTCGATGTCGTTGCGATCAATGAgtg  70
        I  G  R  L  V  P  S  N  A  L  E  V  G  G  V  D  V  V  A  I  N  D
 71  aatggatttgacatcatgcagctcagatgactatctcacaccgcttgtcatgcagCCCGTTCATTGATCT 140
                                                              P  F  I  D  L
141  CGATTACATGgtccgtttattttcagcgcccaccgatcccggaagcgctgacgtgaatctgatctgacgc 210
        D  Y  M
211  tttcgcttacttgcgattgtcttttctttcgatcggtccatgcttagGTCTACATGTTCAAGTACGACTCC 280
                                                       V  Y  M  F  K  Y  D  S
281  GTCCACGGACGCTTCAAGGGCTCCATCGAGGCCAAGGATGGAAAGCTGATCGTTGAGGGGAAGCCGATCC 350
        V  H  G  R  F  K  G  S  I  E  A  K  D  G  K  L  I  V  E  G  K  P  I
351  ACATCTTCGCTGAGAAGGACCCGGCCAACATCCCTTGGGGATCCGTCGGTGCTGACTACGTCGTCGAATC 420
        H  I  F  A  E  K  D  P  A  N  I  P  W  G  S  V  G  A  D  Y  V  V  E  S
421  AACTGGGGTCTTCACCACCATAGACAAGGCTTCAGCTCATCTGAAGGGCGGAGCCAAGAAGGTCGTCATC 490
        T  G  V  F  T  T  I  D  K  A  S  A  H  L  K  G  A  K  K  V  V  I
491  TCTGCCCCCTCCGCCGACGCGCCAATGTTCGTTTGCGGTGTTAACCTTGAAACGTACGATCCAAAGTACA 560
        S  A  P  S  A  D  A  P  M  F  V  C  G  V  N  L  E  T  Y  D  P  K  Y
561  AGGTGgtgagtaggactatcatgagcgcgcacatcccactgagggatttgtgatcctcttgttgtagATT 630
        K  V                                                              I
631  TCGAACGCTTCATGCACGACCAATTGCCT 659
        S  N  A  S  C  T  T  N  C
```

GYLCERALDEHYDE-3-PHOSPHATE DEHYDROGENASE PROMOTER AND HETEROLOGOUS GENE EXPRESSION

FIELD OF THE INVENTION

The invention relates to the discovery of an isolated glyceraldehyde-3-phosphate dehydrogenase promoter in *Pleurotus* and a construct comprising the promoter of the invention operably linked to a heterologous transcribable polynucleotide molecule.

BACKGROUND OF THE INVENTION

In order to enhance the economies of protein production in microorganisms, there have been substantial efforts to improve the efficiency of transcription and translation, maximize the proportion of total protein directed to production of the desired product, enhance the viability of the modified host, and improve the efficiency with which the modified host may be obtained. Using strong promoters to express heterologous genes in appropriate hosts is a major strategy in biotechnological applications. The glyceraldehyde-3-phosphate dehydrogenase (GPD, EC 1.2.1.12) promoter is a strong constitutive promoter which can be induced by any carbon source and has been widely used in the expression of heterologous proteins in *Saccharomyces cerevisiae*, *Pichia pastoris* and other yeasts.

GPD is one of the key enzymes in the glycolytic and gluconeogenesis pathway and comprises up to 5% of the soluble cellular protein content in *S. cerevisiae* and other higher eukaryotes. Furthermore, gpd mRNA accounts for 2~5% of the poly $(A)^+$ RNA present in yeasts. These observations suggest that the gpd gene is regulated by a highly active promoter. In fact, vectors carrying the homologous gpd promoter region have been reported to be efficient in directing expression of heterologous genes in yeasts (Bitter and Egan, 1988, Doring et al., 1998, Eriksson et al., 1995, Vassileva et al., 2001) and filamentous fungi (Juge et al., 1998, Punt et al., 1987). However, known expression vectors containing genetic regulatory elements for expression in filamentous fungi of the ascomycetes class cannot be efficiently expressed in filamentous fungi of the basidiomycetes class.

The gpd genes have also been cloned from basidiomycetous fungi, including *Schizophyllum commune*, *Phanerochaete chrysosporium*, *Agaricus bisporus* (Harmsen et al., 1992), and *Lentinula edodes* (Hirano et al., 1999). Among these mushrooms, genetic transformation using homologous gpd promoter was reported successful only in *A. bisporus*, *Flammulina velutipes* and *L. edodes* (Hirano et al., 2000, Kuo et al., 2004, van de Rhee et al., 1996). Although heterologous promoters have been used for the expression of drug-resistant marker genes, the genetic transformation is not sufficient to express heterologous genes (Ruiz-Diez, 2002). To sufficiently and effectively express a heterologous gene, it is important for a host cell to recognize the promoter sequence by its transcriptional machinery. Chun-Yi Kuo et al. demonstrated that a heterologous gene, hygromycin B phosphotransferase gene (hpt), can be expressed in *F. velutipes* (Kuo et al., 2004). However, it was found that the gpd genes in some basidiomycetous fungi, though highly similar, are significantly different in their promoter regions.

The *Pleurotus* is a well-known edible mushroom. The term "Oyster Mushroom" applies equally to *Pleurotus ostreatus*, *Pleurotus pulmonarius* (which is often paler and appears in the summer), and *Pleurotus populinus* (which is found on the Quaking Aspen). The *Pleurotus* occupies the third position in the worldwide market of industrially produced mushrooms. In addition, the *Pleurotus* produces various secondary metabolites of medical interest.

There is a need to increase the economical and industrial values of the *Pleurotus* by improving the expression of heterologous genes.

SUMMARY OF THE INVENTION

One object of the invention is to provide an isolated promoter comprising a polynucleotide sequence selected from the group consisting of a) a polynucleotide sequence comprising the nucleic acid sequence as shown in SEQ ID NO: 1 or 2; and b) a fragment of the polynucleotide sequence of a) capable of regulating transcription of an operably linked transcribable polynucleotide molecule.

Another object of the invention is to provide a construct comprising the promoter of the invention operably linked to a heterologous transcribable polynucleotide molecule.

A further object of the invention is to provide a transformed mushroom, comprising the construct of the invention.

DETAILED DESCRIPTION OF THE INVENTION

The invention discovers two isolated gpd promoters in *Pleurotus*. These promoters can effectively drive the expression of heterologous genes. With the discovery of these gpd promoters, an expression system can be constructed for the expression of a heterologous gene in mushroom.

According to the invention, the term "isolated" as used herein refers to an isolated nucleic acid molecule that, by the hand of man, exists outside its native environment and is therefore not a product of nature. An isolated nucleic acid molecule may exist in a purified form or in a non-native environment, such as a transgenic host cell.

As used herein, the term "promoter" refers to a polynucleotide molecule that in its native state is located upstream or 5' end to a translational start codon of an open reading frame (or protein-coding region) and that is involved in recognition and binding of RNA polymerase II and other proteins (trans-acting transcription factors) to initiate transcription. When operably linked to a transcribable polynucleotide molecule, a promoter typically causes the transcribable polynucleotide molecule to be transcribed in a manner that is similar to the transcription of the polynucleotide molecule that is normally associated with the promoter. The promoters of the invention can include those produced through the manipulation of known promoters to produce artificial, chimeric, or hybrid ones. Such promoters can also combine cis-elements from one or more promoters, for example, by adding a heterologous regulatory element to an active promoter with its own partial or complete regulatory elements.

As used herein, the term "operatively linked" refers to two nucleic acid sequences that are related physically or functionally. For example, a promoter or regulatory DNA sequence is said to be "associated with" a DNA sequence that codes for a RNA or a protein if the two sequences are operatively linked or so situated that the regulator DNA sequence will affect the expression level of the coding or structural DNA sequence.

As used herein, the term "transcribable polynucleotide molecule" refers to any polynucleotide molecule capable of being transcribed into a RNA molecule.

As used herein, the term "heterologous nucleic acid Sequence" refers to a nucleic acid sequence not naturally associated with the host genome into which it is introduced, including non-naturally occurring multiple copies of a naturally occurring nucleic acid sequence.

As used herein, the phrase "polynucleotide construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecules have been linked in a functionally operative manner. The terms "polynucleotide construct" and "construct" are used interchangeably herein.

As used herein, the term "transformed" refers to a cell, tissue, organ, or organism into which a foreign polynucleotide molecule, such as a construct, has been introduced. Preferably, the polynucleotide molecule introduced is integrated into the genomic DNA of the recipient cell, tissue, organ, or organism so that the introduced polynucleotide molecule is inherited by subsequent progeny.

One object of the invention is to provide an isolated promoter comprising a polynucleotide sequence selected from the group consisting of a) a polynucleotide sequence comprising the nucleic acid sequence as shown in SEQ ID NO: 1 or 2; and b) a fragment of the polynucleotide sequence of a) capable of regulating transcription of an operably linked transcribable polynucleotide molecule. The sequences of SEQ ID NOs: 1 and 2 are shown as follows:

```
                                            SEQ ID NO: 1
AAATCAATGGCAGCCGTTCTTCAGGTGTCATATCTGGTCAGAGTCTCTTG

TGCACTGACCTCCCGATTGGATCTGTGCTGCGACCTCTTCGTTTACCCTC

AGATATATTGTCAGGTTGCCTACGATGTGTATCACGATATCTCAGTGGTA

TGTGGGGGGATATAATCAGTGCGCTAAAAGCGGAATACAGCTCGTCTCCG

TCTTCATCTTAGGCCGAAGTTACAAGAAAGGTGACTAAATGCCGGGACAT

AAGGTATTTCGCATGACGAAACGTCTCCACTCTCAGAGAGTTCGCCCTTT

GCAGGATCTGCTCACACAACTGCTGACATTAGCTAGATCTTGAGTGACCT

TCAGACGATCGCGGCGGGCGTGGGACTTTCAAGATAACGGCGGCATTGAT

CATCTAATCACGCCGTCCTATATAAACCCCTGCCTCCTCTTTCACCCGCA

ATCTCCACTTTCACCACTACCATCCCAGCCCACCCATCCTTTGTAGATAT

GGTGAGTATACCAATATCTATGTACCATATTACACCTCAACCCGTATTCA

GGTCAACGTC

SEQ ID NO: 2
AAATCAATGGCAGCCGTCTCAGGTGTCATATCTGGTACGCTGGAGCAGAG

TCTCTTGTGCCACTGACCTCCCGATTGGATCTGTGCTGCGACCTCTTCGT

TTACCCTCAGATATATTGTCAGGTTGCGTACGATGTGTATCACGATATCT

CAGTGGTGTGTGGGGGGATATAATCAGTGCGCTAAAAGCGGAATACAGCT

CGTCTCCGTCTTCATCTCAGGCCGAAGTTACAAGAAAGGTGACTAAATGC

CGGGACATAAGGTATTTCGCATGACGAAACGTCTCCACTCTCAGAGGATC

TGCTCACACAACTGCTGACATTAGCTAGATCTTGAGACTGAGTGACGATC

GCGGCGGGCGTGGGACTTTCAAGATACGGCGGCATTGATCATCTAATCAC

GCCGTCCTATAAAAACCCCTGCCTCCTCTTTCACCCGCAATCTCCACTTT

CACCACTACCATCCAGCCCACCCATCCTTTGTAAATATGGTGAGCCTACG

AATATCTATGCACCATATTACACCTCAACCCGTATTCAGGTCAACGTC
```

According to the invention, the promoter of the invention can be obtained by using general technology in molecular biology such as cloning, PCR amplification and plasmid constructions etc.

Methods well known to one skilled in the art may be used to identify promoters of interest having activity similar to the promoters described herein. For example, cDNA libraries may be constructed by using cells or tissues of interest and screening them to identify genes having an expression pattern similar to that of the promoters described herein. The cDNA sequence for the identified gene may then be used to isolate the gene's promoter for further characterization. Alternately, transcriptional profiling or electronic northern techniques may be used to identify genes having an expression pattern similar to that of the promoters described herein. Once these genes have been identified, their promoters may be isolated for further characterization. The electronic northern technique refers to a computer-based sequence analysis which allows sequences from multiple cDNA libraries to be compared electronically on the basis of parameters identified by the researcher including abundance in EST populations in multiple cDNA libraries. The transcriptional profiling technique is a high-throughput method used for the systematic monitoring of gene expression profiles for thousands of genes. This DNA chip-based technology arrays thousands of cDNA sequences on a support surface. These arrays are simultaneously hybridized to a population of labeled cDNA probes prepared from RNA samples of different cell or tissue types, allowing direct comparative analysis of expression. This approach may be used for the isolation of regulatory sequences such as promoters associated with those genes.

In another embodiment, the promoter disclosed herein can be modified. Those skilled in the art can create promoters that have variations in the polynucleotide sequence. The polynucleotide sequences of the promoters of the present invention as shown in SEQ ID NO: 1, 2 may be modified or altered to enhance their control characteristics. One preferred method of alteration of a polynucleotide sequence is to use PCR to modify selected nucleotides or regions of sequences. These methods are well known to those of skill in the art. Sequences can be modified by, for example, insertion, deletion, or replacement of template sequences in a PCR-based DNA modification approach. In the context of the present invention, a "variant" is a promoter in which one or more nucleotides of an original promoter is deleted, added, and/or substituted, preferably while substantially maintaining promoter function. For example, one or more base pairs may be deleted from the 5' or 3' end of a promoter to produce a "truncated" promoter. One or more base pairs can also be inserted into, deleted from, or substituted internally in a promoter. In the case of a promoter fragment, variant promoters can include changes affecting the transcription of a minimal promoter to which it is operably linked. A minimal or basal promoter is a polynucleotide molecule that is capable of recruiting and binding the basal transcription machinery. One example of basal transcription machinery in eukaryotic cells is the RNA polymerase II complex and its accessory proteins. Variant promoters can be produced, for example, by standard DNA mutagenesis techniques or by chemically synthesizing the variant promoter or a portion thereof.

Novel chimeric promoters can be designed or engineered by a number of methods. For example, a chimeric promoter may be produced by fusing a first promoter fragment to a second promoter fragment; the resultant chimeric promoter may cause an increase in expression of an operably linked transcribable polynucleotide molecule. Promoters can be constructed so that promoter fragments or elements are operably linked, for example, by placing such a fragment upstream of a minimal promoter. Methods for construction of chimeric and variant promoters of the present invention include, but are not limited to, combining control elements of different promoters or duplicating portions or regions of a promoter. Those of skill in the art are familiar with the standard resource materials that describe specific conditions and procedures of the construction, manipulation, and isolation of macromolecules (e.g., polynucleotide molecules, plasmids, etc.), as well as the generation of recombinant organisms and the screening and isolation of polynucleotide molecules.

According to one embodiment of the invention, a promoter comprising the polynucleotide sequences shown in SEQ ID NO: 1 or 2 includes any length of said polynucleotide sequence that is capable of regulating an operably linked transcribable polynucleotide molecule. For example, the promoters as disclosed in SEQ ID NO: 1 or 2 may be truncated or partially deleted and still be capable of regulating transcription of an operably linked polynucleotide molecule. Any fragments, portions, or regions of the promoters comprising the polynucleotide sequences shown in SEQ ID NO: 1 or 2 can be used as regulatory polynucleotide molecules. Substitutions, deletions, insertions, or any combination thereof can be used to produce a final construct.

Another object of the invention is to provide a construct comprising the promoter of the invention operably linked to a heterologous transcribable polynucleotide molecule. Preferably, the transcribable polynucleotide molecule is operably linked to a 3' transcription termination polynucleotide molecule.

Constructs of the present invention would typically contain a promoter operably linked to a transcribable polynucleotide molecule operably linked to a 3' transcription termination polynucleotide molecule. In addition, constructs may include but are not limited to additional regulatory polynucleotide molecules from the 3'-untranslated region (3' UTR) of the *pleurotus* genes. Constructs may also include but are not limited to the 5' untranslated regions (5' UTR) of an mRNA polynucleotide molecule which can play an important role in translation initiation and can also be a genetic component in a mushroom expression construct. These additional upstream and downstream regulatory polynucleotide molecules may be derived from a source that is native or heterologous with respect to the other elements present on the promoter construct.

Thus, constructs of the present invention comprise promoters such as that provided in SEQ ID NO: 1 or 2, or modified as described above, operatively linked to a transcribable polynucleotide molecule so as to direct transcription of said transcribable polynucleotide molecule at a desired level or in a desired cell.

According to the invention, any suitable heterologous gene can be used as the heterologous transcribable polynucleotide molecule of the invention. Exemplary transcribable polynucleotide molecules for incorporation into constructs of the present invention include, but are not limited to those encoding a) antibodies, including other diagnostic material; b) secondary metabolites, such as lectins; c) therapeutic compounds such as vaccines and steroids; d) biological macromolecules, such as interferon, endostatin and insulin; e) medical enzymes, such as thrombolytics and cerebrosidases; f) genes that confer resistance to pests, disease, or herbicide, such as pesticidal compounds *Bacillus thuringiensis* protein (Bt toxin); g) genes that confer or contribute to a value-added trait, such as modification of nutrient composition or metabolism. Thus, in one preferred embodiment, a polynucleotide molecule of the present invention as shown in SEQ ID NO: 1 or 2 or fragments, variants, or derivatives thereof, capable of regulating transcription, is operably linked to a transcribable polynucleotide molecule that provides a selectable, screenable, or scorable marker. Markers for use in the practice of the present invention include, but are not limited to, transcribable polynucleotide molecules encoding glucuronidase (GUS), green fluorescent protein (GFP), luciferase (LUC), and proteins that confer antibiotic resistance.

Methods are known to introduce constructs of the invention into a cell in such a manner that the transcribable polynucleotide molecule is transcribed into a functional mRNA molecule that is translated and therefore expressed as a protein product. For the practice of the present invention, conventional compositions and methods for preparing and using constructs and host cells are well known to one skilled in the art. Introducing recombinant molecules into cells involve mechanical means such as direct DNA uptake, liposomes, electroporation (Guerche, P. et al.), microinjection (Neuhaus, G. et al.), and use of microprojectiles and a gun or other device to force small particles coated with DNA into cells (Klein, T. M. et al.).

A further object of the invention is to provide a transformed mushroom containing the construct of the invention.

A transformation construct containing a promoter of the present invention may be introduced into mushrooms by any transformation method. Methods and materials for transforming mushrooms by introducing a mushroom expression construct into a mushroom genome in the practice of this invention can include any of the well-known and demonstrated methods including electroporation, *Agrobacterium*-mediated transformation and protoplast transformation. Preferably, the mushroom is selected from the group consisting of *Flammulina, Agaricus, Pleurotus* and *Lentinula*. More preferably, the mushroom is selected from the group consisting of *Pleurotus ostreatus, Pleurotus pulmonarius*, and *Pleurotus populinus*. Most preferably, the mushroom is *Pleurotus ostreatus*.

The following examples are included to demonstrate preferred embodiments of the present invention. It should be appreciated by those of skill in the art that the techniques disclosed in the examples that follow represent techniques discovered by the inventors to function well in the practice of the present invention. However, those of skill in the art should, in light of the present disclosure, appreciate that many changes can be made in the specific embodiments that are disclosed and still obtain a similar result without departing from the spirit and scope of the present invention. Therefore all matter set forth or shown in the accompanying drawings is to be interpreted as illustrative and not limiting.

EXAMPLE

Example 1

Cloning of Promoter and Gene of Glyceraldehyde-3-phosphate Dehydrogenase

Strains and Media

*P. ostreatus* BCRC 36249 was purchased from the Bioresources Collection and Research Center (Hsinchu, Taiwan) and grown in either PDA (Potato dextrose agar, Difco, Detroit, Mich., USA) or PDB (Potato dextrose broth, Difco) at 25° C. Transformants were selected from PDA with 30 g/ml of hygromycin (A.G. Scientific, Inc., San Diego, Calif., USA). The *Escherichia coli* strain DH5 (GIBCOBRL, Life Technologies, Grand Island, N.Y., USA) was used for DNA manipulations and grown in LB medium (Sigma Chem. Co., St. Louis, Mo., USA) at 37° C. PCR amplified DNA fragments were purified and then cloned into pGEM-T Easy vector (Promega, Madison, Wis., USA) and sequenced.

Cloning of the gpd Gene

Figure 1:
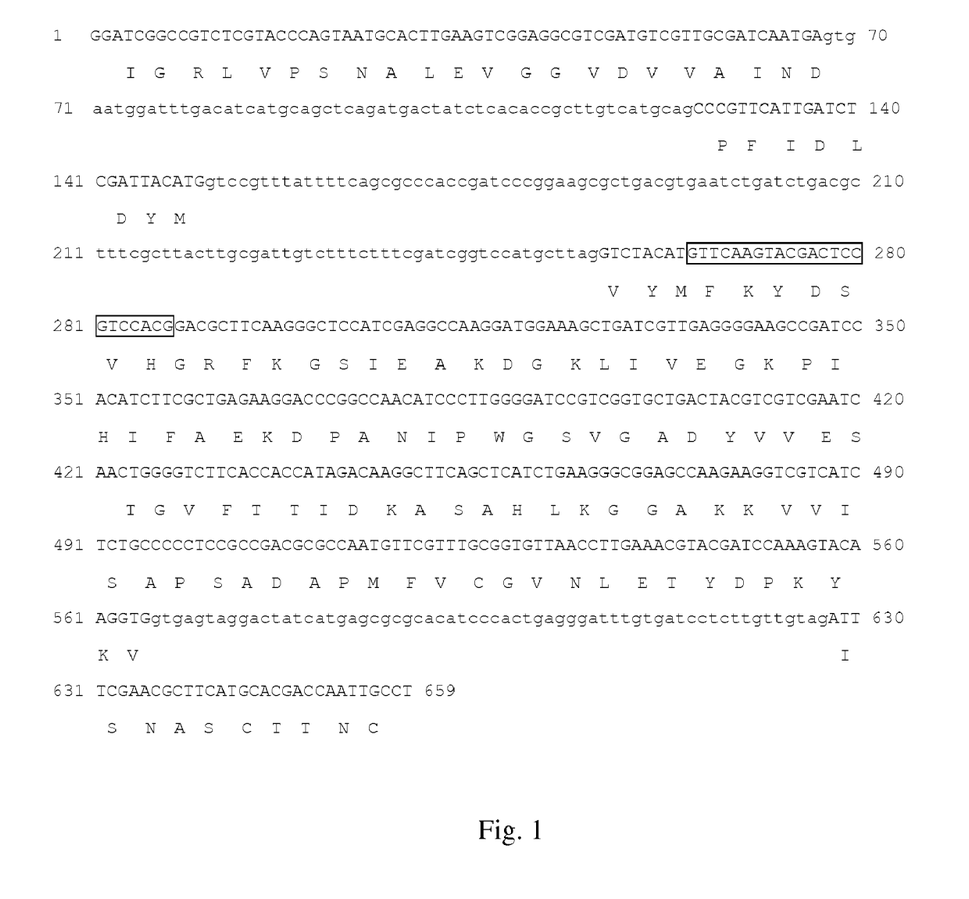
FIG. 1 shows the sequence of partial gpd of *P. ostreatus*.

Two degenerate primers, 5'GKATCGGMCGYMYYGT-MYYCMGHAATGC 3' corresponding to RIGRIVLRNA and 5'ARGCARTTGGTHGTGCAHGAAGCRTTYG 3' corresponding to SNASCTTNCL, were designed according to the conserved amino-acid sequences of published basidiomycetous gpd genes. (GenBank accession nos. AF515622, BAA83550, AAA33926, AAA33732, AAA32634, AAA32633). By using these degenerate primers and *P. ostreatus* genomic DNA as the template, partial gpd of *P. ostreatus* was cloned through PCR amplification (see FIG. 1).

Figure 2:
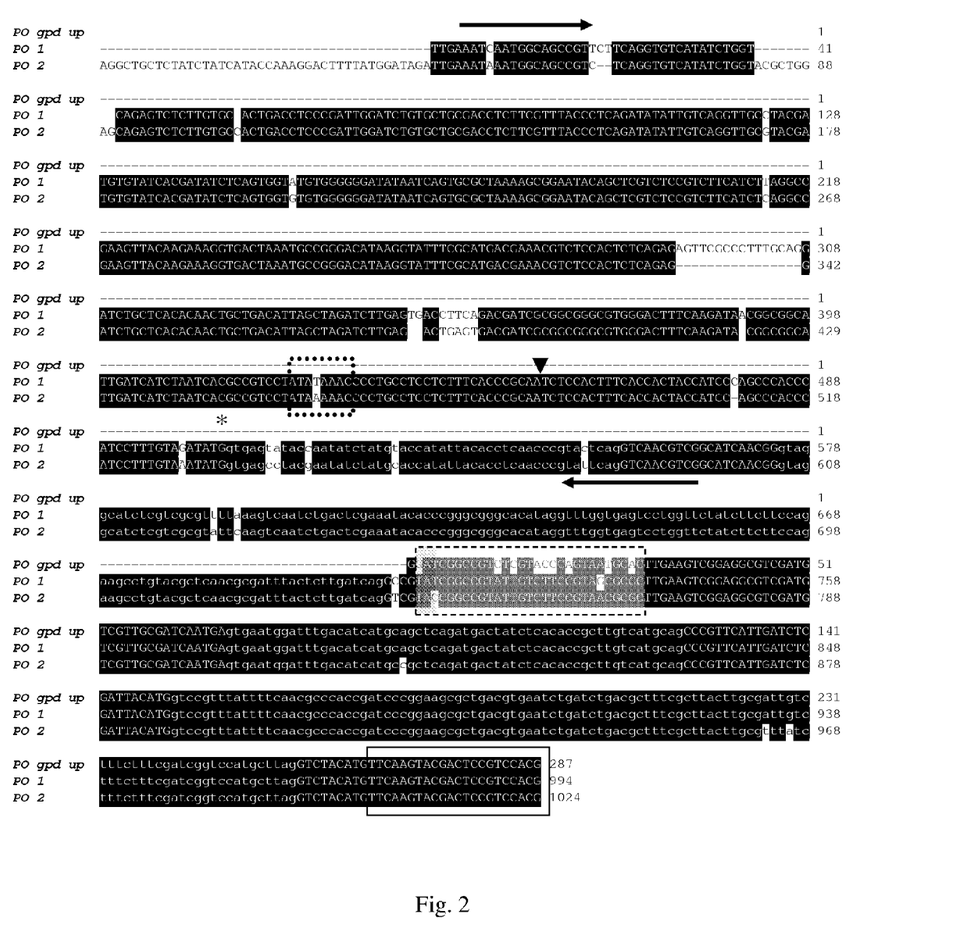
FIG. 2 shows the sequences of the two copies of gpd in the genome of *P. ostreatus*.

The 5'-flanking region and cDNA of *P. ostreatus* gpd was cloned by "Rapid Genome Walking" (Kilstrup and Kristiansen, 2000) and SMART™ RACE cDNA Amplification Kit (BD Bioscience, Paolo Alto, Calif., USA) Gene-specific primer (GSP) was designed on the basis of the partial *P. ostrestus* gpd sequence. Using degenerate primers designed according to conserved amino-acid sequences of published basidiomycetous gpd genes, a fragment of approximately 0.6 kb in size was amplified by PCR from the *P. ostreatus* genomic DNA template. By using GSP and rapid genome walking, two PCR products of 1.0 kb in size were obtained. Differences between sequences indicated there were at least two copies of gpd in the genome of *P. ostreatus* (see FIG. 2). After sequencing, one copy of gpd had 994 base pairs (named as PO 1) and the other 1024 base pairs (named as PO2). The 5'-flanking regions of these two *P. ostreatus* gpd genes were obtained by aligning sequences of cDNA and genome walking products.

Example 2

Construction of the Promoter of the Invention and a Heterologous Polynucleotide and Transformation of the Construct Plasmid Construction The hygromycin B phosphotransferase (hpt) gene with cauliflower mosaic virus (CaMV) 35S terminator was amplified from pCAMBIA 1300 (CAMBIA, Canberra, Australia), then the amplified fragment was cloned into pGEM-T Easy vector and two 0.6 kb promoter regions of the *P. ostrestus* gpd gene were introduced to drive hpt gene expression. Two resulting plasmids pPOH1 and pPOH2 were used for the transformation experiments.

Figure 3:
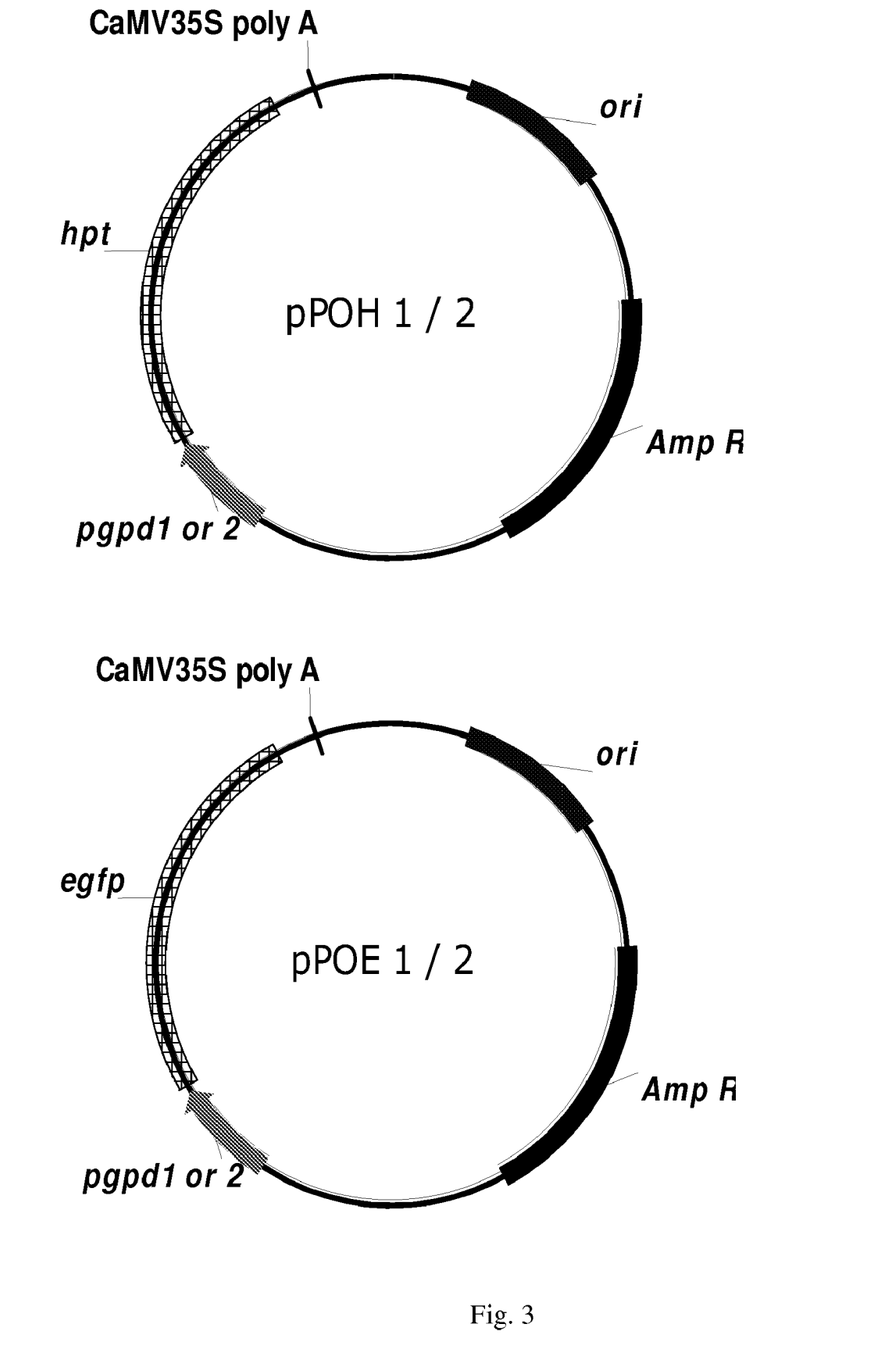
FIG. 3 shows the restriction maps of the plasmids pPOH1 and pPOH2.

For the expression of reporter gene egfp, plasmids pPOH1 and pPOH2 were used as backbones; egfp substituted hpt to construct pPOE1 and pPOE2. Details of the primers used are illustrated in Table 1 below. egfp were amplified from pHygEGFP (BD Bioscience, Palo Alto, Calif., USA). The resulting plasmids (FIG. 3) were used for all study-reported transformation experiments.

TABLE 1

Primers used in plasmids construction

| Target genes | Primers used | Usage |
|---|---|---|
| *P. ostrestus* pgpd | pPG-f (5' AAATCAATGGCAGCCGT 3') (SEQ ID NO:3) | Forward primer for pgpd cloning. |
| | pPG-ir (5' GACGTTGACCTGAATACG 3') (SEQ ID NO:4) | Reverse primer for pgpd cloning with the 1$^{st}$ intron of gpd. |
| hpt | hpt-f (5' ATGAAAAAGCCTGAACTCACC 3') (SEQ ID NO:5) | Forward primer for amplification of hpt. |
| | hpt-r (5' ACAACTTAATAACACATTGCG 3') (SEQ ID NO:6) | Reverse primer for amplification of hpt. |
| egfp | Egfp-f (5' ATGGTGAGCAAGGGCG 3') (SEQ ID NO:7) | Forward primer for amplification of egfp. |
| | Egfp-r (5' CTTGTACAGCTCGTCCATGCC 3') (SEQ ID NO:8) | Reverse primer for amplification of egfp. |

Transformation Procedure

Transformation of *P. ostrestus* was undertaken on the basis of a modification of the technique reported in a previous study (Kuo et al., 2004). Basidiospores were collected from *P. ostrestus* fruit bodies and suspended in PDB then incubated overnight with gentle shaking at 25° C. These germinated basidiospores were harvested by centrifugation at 2000 g for 5 min and resuspended in P buffer (0.02 M phosphate buffer, pH 5.8, 0.6 M mannitol) containing 3 mg/ml lysing enzymes (Sigma). After incubation for 2 h, these basidiospores were washed free of enzyme and transferred to a small volume of electroporation buffer (1 mM HEPES, pH 7.5, 0.6 M mannitol). Basidiospores ($10^7$-$10^8$) were mixed with 10 μg plasmid DNA, chilled on ice for 10 min, and subjected to electroporation. Electroporation was performed by BTX ECM 630 using 0.2-cm cuvettes (BTX, San Diego, Calif., USA) with an electric-pulse delivery setting of 25 µF for the capacitor; 100Ω for the resistor and a 12.5 kV/cm setting for the field strength. Transformants were selected from PDA plates containing 30 µg/ml hygromycin.

Basidiospores transformed either with pPOH1 or pPOH2 could colonize on PDA with 30 g/ml hygromycin, which indicated that both promoters could drive downstream gene expression. The transformation efficiency was of the order of five to 20 transformants per µg DNA while no hygromycin-resistant colonies were observed in the control experiment without adding plasmid DNA. As far as we were able to determine, no significant difference in growth rate or morphology existed between transformants and the wild-type strain. This report was the first transformation protocol for *P. ostreatus* without troublesome protoplast preparation.

Subculturing transformants on media without selection pressure and followed by hygromycin-resistant test demonstrated that hygromycin resistance trait remained stable during mitotic cell division for five months. These two gpd promoters of *P. ostreatus* that constitutively drove hygromycin resistance trait indicated the promise of downstream gene expression. The presence of hpt DNA introduced via transformation was checked by PCR amplification. No false positives were detected by PCR amplification in 50 antibiotic-resistant cultures.

Detection of EGFP in Transformants

EGFP transformants were screened by a fluorescent microscope (E600, Nikon, Tokyo, Japan) fitted with a Nikon B-2A filter (450-490 nm excitation filter; 505 nm dichroic filter; 520 nm barrier filter).

Western Hybridization

For western analysis of EGFP, transformants and the wild-type strain were cultured for seven days in PDB. Mycelia were collected and subsequently ground in liquid nitrogen using a mortar and pestle. A total of 50 mg mycelial powder was mixed with 1 ml protein-extraction buffer (50 mM sodium phosphate, pH=7.4, 1 mM PMSF, 0.1% Triton X-100, 0.5M NaCl) and chilled on ice for 5 min. After centrifugation at 13,000 g for 20 min, supernatant was collected as total cellular protein. Samples were separated by 10% sodium dodecyl sulfatepolyacrylamide gel electrophoresis (SDS-PAGE) and transferred to PVDF sequencing membrane (Millipore, Bedford, Mass., USA) using a semi-dry blotting system (Genmedika, Taipei, Taiwan). The detection of EGFP was carried out by using a (1:8,000) monoclonal anti-GFP living-colors peptide antibody (BD Bioscience) and with the BCIP/NBT western detection kit (PerkinElmer, Boston, Mass., USA), using a procedure described by the manufacturers.

Quantification of EGFP by ELISA

A sandwich ELISA for EGFP was conducted on 100 µl of each protein extract. Samples were incubated for 1 h on ELISA plates (PerkinElmer, Boston, Mass.) coated with monoclonal EGFP antibody (Abcam, Cambridge, UK). (Each sample was repeated in triplicate for each plate.) Rabbit anti-GFP polyclonal antibody (Abcam, Cambridge, UK) was added to each well at a 1:10,000 dilution and incubated for 1 h at 4° C. Goat polyclonal antibodies against rabbit IgG conjugated to HRP enzyme (PerkinElmer, Boston, Mass.) were added to each well at a 1:5,000 dilution and incubated for 1 h at 4° C. To each well, 100 µl of HRP substrate (BioFX, MD) was added. After 5 min, 50 µl of 1.0 M $H_2SO_4$ was added to stop the reaction. The absorbance at 450 nm was measured for each well using a 96-well plate reader (VERSAmax, Sunnyvale, Calif.). Protein concentrations were determined by using a bicinchoninic acid assay (Pierce, Dallas, Tex.). The EGFP expressed in *E. coli* by pET21a(+) serves as standards. A standard curve was calculated on the basis of the averaged values of the standards and used to estimate the amount of EGFP in the extract samples. The estimated EGFP values from ELISA method were reported as milligrams EGFP per gram total soluble protein.

The presence of an intron for egfp expression in some basidiomycetes has been reported (Burns et al., 2005; Lugones et al., 1999; Ma et al., 2001). Therefore, herein, the promoter region with the first intron of the gpd gene was tested as a potential vehicle to drive egfp. About 80% of *P. ostreatus* transformants prepared with the first intron exhibited green fluorescence. The expression of egfp was able to remain stable after multiple rounds of subculture in the absence of any selection pressure. By contrast, no expression was observed in the construct prepared without the first intron region (data not shown). Such results indicated that the presence of the 5' intron is required for egfp expression within *P. ostreatus*.

Figure 4:
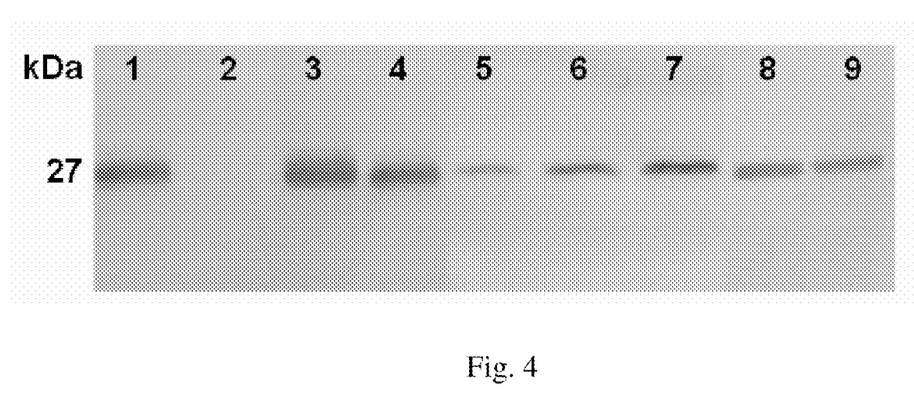
FIG. 4 shows the western plot of the expression of egfp.

The expression of egfp was also confirmed by western hybridization, as shown in FIG. 4. Immunoblotting with the monoclonal anti-GFP antibody detected a 27-kDa polypeptide present in the positive control (Lane 1) and also in the total cellular protein derived from the transformant (Lanes 3-9), whereas no signal was detected in the untransformed strain (Lane 2).

The average amount of EGFP in the extract samples ranged from 0.4 to 5 mg per gram of total soluble protein from different transformants. The percentage of EGFP in total soluble protein was $5.4 \times 10^{-3}$ (0.5%) for the transformant with the highest EGFP expression level.

REFERENCES

1. Bitter, G. A., Egan, K. M., 1988. Expression of interferon-gamma from hybrid yeast GPD promoters containing upstream regulatory sequences from the GAL1-GAL10 intergenic region. Gene. 69, 193-207.
2. Doring, F., Klapper, M., Theis, S., Daniel, H., 1998. Use of the glyceraldehyde-3-phosphate dehydrogenase promoter for production of functional mammalian membrane transport proteins in the yeast *Pichia pastoris*. Biochem Biophys Res Commun. 250, 531-535.
3. Eriksson, P., Andre, L., Ansell, R., Blomberg, A., Adler, L., 1995. Cloning and characterization of GPD2, a second gene encoding sn-glycerol 3-phosphate dehydrogenase (NAD+) in *Saccharomyces cerevisiae*, and its comparison with GPD1. Mol. Microbiol. 17, 95-107.
4. Guerche, P. et al., 1987, *Plant Science* 52: 111-116.
5. Harmsen, M. C., Schuren, F. H., Moukha, S. M., van Zuilen, C. M., Punt, P. J., Wessels, J. G., 1992. Sequence analysis of the glyceraldehyde-3-phosphate dehydrogenase genes from the basidiomycetes *Schizophyllum commune, Phanerochaete chrysosporium* and *Agaricus bisporus*. Curr Genet. 22, 447-454.
6. Hirano, T., Sato, T., Okawa, K., Kanda, K., Yaegashi, K., Enei, H., 1999. Isolation and characterization of the glyceraldehyde-3-phosphate dehydrogenase gene of *Lentinus edodes*. Biosci Biotechnol Biochem. 63, 1223-1227.
7. Hirano, T., Sato, T., Yaegashi, K., Enei, H., 2000. Efficient transformation of the edible basidiomycete *Lentinus edodes* with a vector using a glyceraldehyde-3-phosphate dehydrogenase promoter to hygromycin B resistance. Mol Gen Genet. 263, 1047-1052.

8. Juge, N., Svensson, B., Williamson, G., 1998. Secretion, purification, and characterisation of barley alpha-amylase produced by heterologous gene expression in *Aspergillus niger*. Appl Microbiol Biotechnol. 49, 385-392.
9. Kilstrup, M., Kristiansen, K. N., 2000. Rapid genome walking: a simplified oligo-cassette mediated polymerase chain reaction using a single genome-specific primer. Nucleic Acids Res. 28, E55.
10. Klein, T. M. et al., 1987, Nature 327:70-73.
11. Kuo, C. Y., Chou, S. Y., Huang, C. T., 2004. Cloning of glyceraldehyde-3-phosphate dehydrogenase gene and use of the gpd promoter for transformation in *Flammulina velutipes*. Appl Microbiol Biotechnol. 65, 593-599.
12. Neuhaus, G. et al., 1987, Theor. Appl. Genet. 75:30-36.
13. Punt, P. J., Oliver, R. P., Dingemanse, M. A., Pouwels, P. H., van den Hondel, C. A., 1987. Transformation of *Aspergillus* based on the hygromycin B resistance marker from *Escherichia coli*. Gene. 56, 117-124.
14. Ruiz-Diez, B., 2002. Strategies for the transformation of filamentous fungi. J Appl Microbiol. 92, 189-195.
15. van de Rhee, M. D., Graca, P. M., Huizing, H. J., Mooibroek, H., 1996. Transformation of the cultivated mushroom, *Agaricus bisporus*, to hygromycin B resistance. Mol Gen Genet. 250, 252-258.
16. Vassileva, A., Chugh, D. A., Swaminathan, S., Khanna, N., 2001. Expression of hepatitis B surface antigen in the methylotrophic yeast *Pichia pastoris* using the GAP promoter. J. Biotechnol. 88, 21-35.

What is claimed is:

1. An isolated promoter comprising a polynucleotide sequence selected from the group consisting of a) a polynucleotide sequence comprising the nucleic acid sequence as shown in SEQ ID NO: 1 or 2; and b) a fragment of the polynucleotide sequence of a) capable of regulating transcription of an operably linked transcribable polynucleotide molecule.

2. A construct comprising the promoter of claim 1 operably linked to a heterologous transcribable polynucleotide molecule.

3. The construct of claim 2, wherein the transcribable polynucleotide molecule is operably linked to a 3' transcription termination polynucleotide molecule.

4. The construct of claim 2, wherein said transcribable polynucleotide molecule is a gene encoding an antibody, a secondary metabolite, a therapeutic compound, a biological macromolecule, a medical enzyme; a gene that confers resistance to pests, diseases, or herbicides; or a gene that confers or contributes to a value-added trait.

5. The construct of claim 4, wherein said secondary metabolite is a lectin, said therapeutic compound is a vaccine, said biological macromolecule is an interferon, endostatin or insulin, said medical enzyme is thrombolytic or cerebrosidase and said gene that confers resistance to pests, diseases, or herbicides is a pesticidal compound *Bacillus thuringiensis* protein (Bt toxin).

6. The construct of claim 2, wherein said transcribable polynucleotide molecule is a marker gene.

7. The construct of claim 2, wherein said transcribable polynucleotide molecule is a green fluorescence gene.

8. A transformed cell, comprising the construct of claim 2.

9. A transformed mushroom, comprising the construct of claim 2.

10. The transformed mushroom of claim 9, wherein the mushroom is selected from the group consisting of *Flammulina, Agaricus, Pleurotus* and *Lentinula*.

11. The transformed mushroom of claim 9, wherein the mushroom is selected from the group consisting of *Pleurotus ostreatus, Pleurotus pulmonarius*, and *Pleurotus populinus*.

12. The transformed mushroom of claim 9, wherein the mushroom is *Pleurotus ostreatus*.

13. A method of directing expression of a transcribable polynucleotide sequence in a mushroom cell operably linking the promoter of claim 1 to the polynucleotide sequence and transforming a mushroom cell with the promoter operably linked to the polynucleotide sequence.

14. The method of claim 13, wherein the mushroom is selected from the group consisting of *Flammulina, Agaricus, Pleurotus* and *Lentinula*.

15. The method of claim 13, wherein the mushroom is selected from the group consisting of *Pleurotus ostreatus, Pleurotus pulmonarius*, and *Pleurotus populinus*.

16. The method of claim 13, wherein the mushroom is *Pleurotus ostreatus*.

* * * * *

SEQUENCE LISTING

<160> NUMBER OF SEQ ID NOS: 8

<210> SEQ ID NO 1
<211> LENGTH: 560
<212> TYPE: DNA
<213> ORGANISM: Pleurotus ostreatus

<400> SEQUENCE: 1

```
aaatcaatgg cagccgttct tcaggtgtca tatctggtca gagtctcttg tgcactgacc      60
tcccgattgg atctgtgctg cgacctcttc gtttaccctc agatatattg tcaggttgcc     120
tacgatgtgt atcacgatat ctcagtggta tgtgggggga tataatcagt gcgctaaaag     180
cggaatacag ctcgtctccg tcttcatctt aggccgaagt tacaagaaag gtgactaaat     240
gccgggacat aaggtatttc gcatgacgaa acgtctccac tctcagagag ttcgcccttt     300
gcaggatctg ctcacacaac tgctgacatt agctagatct tgagtgacct tcagacgatc     360
gcggcgggcg tgggactttc aagataacgg cggcattgat catctaatca cgccgtccta     420
tataaacccc tgcctcctct ttcacccgca atctccactt tcaccactac catcccagcc     480
cacccatcct ttgtagatat ggtgagtata ccaatatcta tgtaccatat tacacctcaa     540
cccgtattca ggtcaacgtc                                                 560
```

<210> SEQ ID NO 2
<211> LENGTH: 548
<212> TYPE: DNA
<213> ORGANISM: Pleurotus ostreatus

<400> SEQUENCE: 2

```
aaatcaatgg cagccgtctc aggtgtcata tctggtacgc tggagcagag tctcttgtgc      60
cactgacctc ccgattggat ctgtgctgcg acctcttcgt ttaccctcag atatattgtc     120
aggttgcgta cgatgtgtat cacgatatct cagtggtgtg tgggggata taatcagtgc     180 gctaaaagcg gaatacagct cgtctccgtc ttcatctcag gccgaagtta caagaaaggt     240
gactaaatgc cgggacataa ggtatttcgc atgacgaaac gtctccactc tcagaggatc     300
tgctcacaca actgctgaca ttagctagat cttgagactg agtgacgatc gcggcgggcg     360
tgggactttc aagatacggc ggcattgatc atctaatcac gccgtcctat aaaaacccct     420
gcctcctctt tcacccgcaa tctccacttt caccactacc atccagccca ccatcctttt    480
gtaaatatgg tgagcctacg aatatctatg caccatatta cacctcaacc cgtattcagg     540
tcaacgtc                                                              548
```

-continued

```
<210> SEQ ID NO 3
<211> LENGTH: 17
<212> TYPE: DNA
<213> ORGANISM: Artificial
<220> FEATURE:
<223> OTHER INFORMATION: primer

<400> SEQUENCE: 3
aaatcaatgg cagccgt                                                    17

<210> SEQ ID NO 4
<211> LENGTH: 18
<212> TYPE: DNA
<213> ORGANISM: Artificial
<220> FEATURE:
<223> OTHER INFORMATION: primer

<400> SEQUENCE: 4
gacgttgacc tgaatacg                                                   18

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
atgaaaaagc ctgaactcac c                                               21

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
acaacttaat aacacattgc g                                               21

<210> SEQ ID NO 7
<211> LENGTH: 16
<212> TYPE: DNA
<213> ORGANISM: Artificial
<220> FEATURE:
<223> OTHER INFORMATION: primer

<400> SEQUENCE: 7
atggtgagca agggcg                                                     16

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
cttgtacagc tcgtccatgc c                                               21
```